United States Patent [19]

Moore

[11] Patent Number: 4,709,481

[45] Date of Patent: Dec. 1, 1987

[54] SHAVING TOOL

[76] Inventor: Milton D. Moore, 2940 Holly Hall, Houston, Tex. 77054

[21] Appl. No.: 897,871

[22] Filed: Aug. 19, 1986

[51] Int. Cl.$^4$ ............................................. B26B 9/02
[52] U.S. Cl. ......................................... 30/356; 30/314; 128/305; 128/314; 128/329 R
[58] Field of Search ................. 30/356, 345, 346, 314, 30/353, 165, DIG. 8; 128/305 R, 329 R, 314

[56] References Cited

U.S. PATENT DOCUMENTS 1,089,019  3/1914  Swasey .............................. 30/353 X
3,035,344  5/1962  Brown ................................... 30/346
4,098,157  7/1978  Doyle .............................. 128/305 X

FOREIGN PATENT DOCUMENTS 2411049  9/1975  Fed. Rep. of Germany ........ 30/356

Primary Examiner—Douglas D. Watts
Attorney, Agent, or Firm—William E. Shull; Gregory L. Maag; Eric P. Mirabel

[57] ABSTRACT

There is disclosed herein an instrument for use in efficiently and sanitarily extricating an ingrown hair from the skin, the instrument comprising an elongate handle and a tip attached to the handle, wherein the tip comprises a curved and tapered blade.

16 Claims, 5 Drawing Figures

SHAVING TOOL

BACKGROUND OF THE INVENTION

The present invention relates generally to a device for use in remedying psueudofoliculitis barbae (hereinafter PFB) or ingrown hairs. More particularly, the present invention relates to a device used for freeing the ingrown portion of a PFB so that it can be shaved by a conventional razor or shaver. Still more particularly, the present invention relates to an instrument used to lift an exposed portion of the PFB so as to free the end of the ingrown hair from the dermal or epidermal layers of skin, and an instrument used to pierce the skin when necessary to extricate an unexposed PFB.

A PFB results when the end of a hair growing from a hair follicle grows inwardly back toward and into the epidermal or dermal layers of skin, or both. When this oocurs, a portion of the PFB may be exposed, or the entire PFB may remain beneath the epidermal layers of skin. In either of such manifestations, a PFB can cause an uncomfortable and inflammatory reaction. A PFB which grows out of the epidermal layer and then turns and grows back into the skin may result in the formation of a papule and irritate and inflame the surrounding skin tissue. A PFB which does not penetrate the epidermal layer of skin, but instead grows entirely thereunder, may form a pustule, another condition which can become inflamed and be very painful to the sufferer.

In U.S. patent application Ser. No. 06/822,608, filed Jan. 27, 1986, entitled "Medicated Shaving Cream and Method for Using Same", the entire disclosure of which is incorporated herein by reference, there is disclosed a new and unique medicated shaving cream and a method for using the shaving cream to treat PFB. As described therein, an elongate object may be used by inserting it under a portion of the PFB and lifting the PFB to free the non-rooted end from the dermal or epidermal layers of skin.

In the past, to remedy a PFB, ordinary household tweezers were often employed. While tweezers could be used to remove the ingrown portion of a PFB where a portion of the hair was exposed, tweezers were generally ineffective in those instances where the PFB grew entirely under the skin. Even in those instances where a portion of the PFB was exposed, it was often hard to grasp. Furthermore, often while using tweezers to extricate a PFB, the entire hair was pulled out of its follicle, leaving the empty follicle subject to infection. For the wellbeing of the PFB sufferer, it is not advisable to remove the entire hair, but is medically preferably to simple extricate the non-rooted end of the PFB so that it can be shaved along with the surrounding hairs.

In the past it has also been common to use a needle or straight pin in attempting to extricate the end of a PFB from the skin. Such needles and pins, however, provided no means by which to grasp the hair. The use of a needle or pin was additionally unsatisfactory since it often caused painful wounds to the PFB sufferer as the pustule or papule was probed or lanced by the needle or pin. The use of needles and pins is further unsatisfactory because these devices can easily be accidentally inserted into the skin to a painful depth, due to their extremely sharp point and narrow cross section. Finally, such needles and pins are often not kept in a sanitary condition. As a result, the person desiring to extricate a PFB often uses an unsanitized pin or needle found in a sewing kit, household drawer, or other catch-all compartment.

SUMMARY OF THE INVENTION

To overcome the problems associated with PFB removal as described generally above, there is described herein an effective and sanitary instrument for use in extricating the non-rooted end of a PFB from the epidermal or dermal layers of the skin, or both, the instrument of the present invention being an improvement in efficiency, sanitation, and safety over the devices previously known or used.

The instrument of the present invention comprises an elongate handle and a tip attached to the handle, the tip comprising a proximal portion and a distal portion, with the distal portion forming a curved and tapered blade.

The elongate handle may comprise an upper surface, a lower surface, and two side surfaces, the surfaces intersecting so as to define a generally square or rectangular cross section. The proximal portion of the tip includes an upper concave surface having a radius R, a lower surface that is coplanar with the lower surface of the handle, and two side surfaces, each of which is coplanar with one of the side surfaces of the handle. The distal portion of the tip of the present invention comprises a blade, which may include an upper concave surface having a radius R and being continuous with the upper concave surface of the proximal portion of the tip. Additionally, the blade may include two upper side surfaces and two lower convex surfaces, the two lower convex surfaces intersecting in a curved crown. Each of the upper side surfaces of the blade may intersect the upper concave surface and one of the lower convex surfaces, such that the intersection of the upper concave surface, the lower convex surfaces, and the upper side surfaces is a sharp point. This point may be formed at a predetermined distance above the plane which includes the upper surface of the elongate handle. Additionally, the radius R of the concave surface of the proximal and distal portions of the tip may be equal to the radius of the curved crown formed by the intersection of the two lower convex surfaces of the blade. Finally, the entire instrument may be injection molded of sanitary, non-toxic, hypoallergenic, and inexpensive plastic.

Thus, the present invention comprises an instrument suitable for extricating the non-rooted end of a PFB in a sanitary and efficient manner, and in a manner which does not uproot and remove the entire PFB which might exacerbate any inflammation or infection already present, or which might leave an open hair follicle susceptible to infection. These and various other characteristics and advantages of the present invention will become readily apparent to those skilled in the art upon reading the following detailed description and claims, and by referring to the accompanying drawings.

BRIEF DESCRIPTION OF THE DRAWINGS

For a more detailed description of the preferred embodiment of the invention, reference will now be made to the accompanying drawings, wherein.

DESCRIPTION OF THE PREFERRED EMBODIMENT

Figure 1:
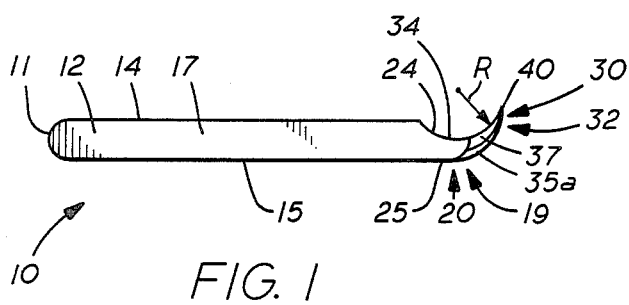
FIG. 1 depicts a side elevation of an instrument constructed according to the principles of the present invention.

Referring now to FIG. 1, there is depicted an instrument 10 constructed in accordance with the present invention and useful for remedying a PFB by extricating the non-rooted end of the PFB from the layers of skin in which it has grown. More particularly, the instrument 10 comprises an elongate handle 12, generally square or rectangular in cross section, formed by upper surface 14, lower surface 15, and side surfaces 16 and 17, side surfaces 16 and 17 best shown in FIG. 3.

The instrument 10 further comprises a tip 19 which includes a proximal portion 20 and a distal portion 30. The proximal portion 20 comprises an upper concave surface 24 having radius R, and a lower surface 25, the lower surface 25 being coplanar with lower surface 15 of handle 12. The proximal portion further comprises side surfaces 26 and 27, best shown in FIG. 3, side surfaces 26 and 27 being coplanar with side surfaces 16 and 17, respectively, of handle 12.

Figure 2:
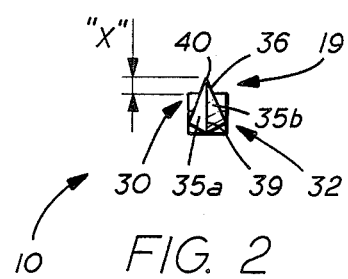
FIG. 2 depicts a front elevation of the instrument depicted in FIG. 1.

Distal portion 30 of tip 19 forms a blade 32, blade 32 including an upper concave surface 34 of radius R which is contiguous with or an extension of upper concave surface 24 of proximal portion 20 of tip 19. Additionally, blade 32 comprises two lower convex surfaces 35a and 35b, as shown in FIG. 2. The two lower convex surfaces 35a and 35b intersect in a curved crown 39.

Figure 3:
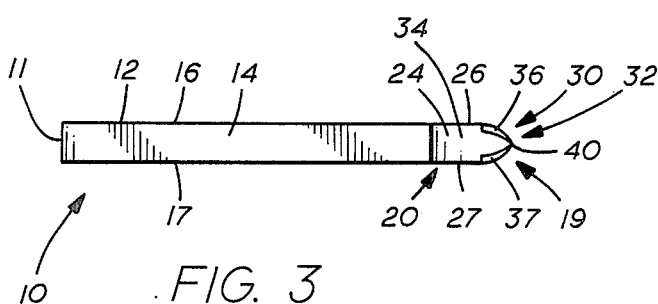
FIG. 3 depicts a top view of the instrument depicted in FIG. 1.

Blade 32 further comprises upper side surfaces 36 and 37, as shown in FIGS. 1, 2, and 3. Side surfaces 36 and 37, lower convex surfaces 35a and 35b, and upper surface 34 all intersect in a sharp point 40 located at a distance "X" above the plane which includes the upper surface 14 of the handle 12.

The entire instrument 10 can be injection molded of nontoxic, hypoallergenic plastic. Point 40 is formed so as to be sharp enough to pierce the skin, but not so sharp as to be likely to penetrate the skin to a dangerous depth. Accordingly, the angles formed by the intersections of the planes which include upper side surfaces 36 and 37 of blade 32 with the planes which include side surfaces 16 and 17, respectively, of handle 12 are preferably less than 30 degrees, about 25 degrees being preferred. When point 40 dulls, the entire instrument may be disposed of since the low cost of suitable plastics for making the present invention permits a low manufacturing cost and thus a low purchase price to the consumer. Of course, it should be understood that materials other than plastic can be used for this invention, such as stainless steel, but in that event the instrument might not be regarded as disposable.

An instrument 10 of the preferred embodiment has been constructed and proved to work satisfactorily where the instrument 10 has an overall length of about 3 inches, the handle 12 has a generally square or rectangular cross section of about one-quarter inch by one-quarter inch, and the tip comprises a curved blade with an upper surface of radius about 0.312 inches and two lower convex surfaces intersecting in a curve or crown also having a radius of about 0.312 inches. The instrument so constructed was injection molded of plastic, point 40 being located at a distance of about 0.062 inches above the plane which includes the upper surface of the elongate handle 12. The blade was molded so that the planes including the upper side surfaces 36, 37 of the tip or blade intersected the planes including the side surfaces of the handle at an angle of about 25 degrees.

Figure 4:
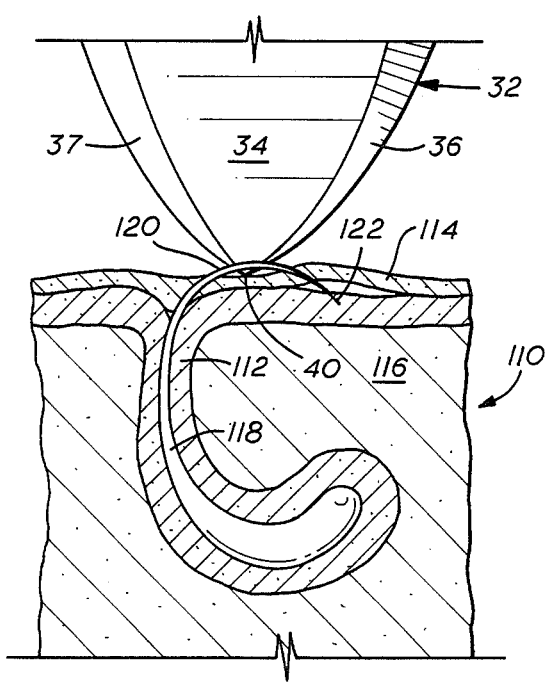
FIG. 4 depicts a cross sectional view of an area of skin having one form of PFB being extricated by the instrument depicted in FIG. 1.

Referring now to FIG. 4, there is shown an instrument 10 of the present invention being used to extricate from the skin the end of a PFB which is partially exposed. Shown generally is a section of skin 110 which is comprised of epidermis 114 and dermis 116. A hair follicle 112 and hair 118 are also depicted in FIG. 4. In use, point 40 of blade 32 is inserted under the exposed section 120 of hair 118. The exposed section 120 of hair 118 contacts upper surface 34 or side surfaces 36 or 37 of blade 32 and the ingrown portion 122 of hair 118 is extricated as the instrument 10 is pulled or pried upward and away from the skin.

Figure 5:
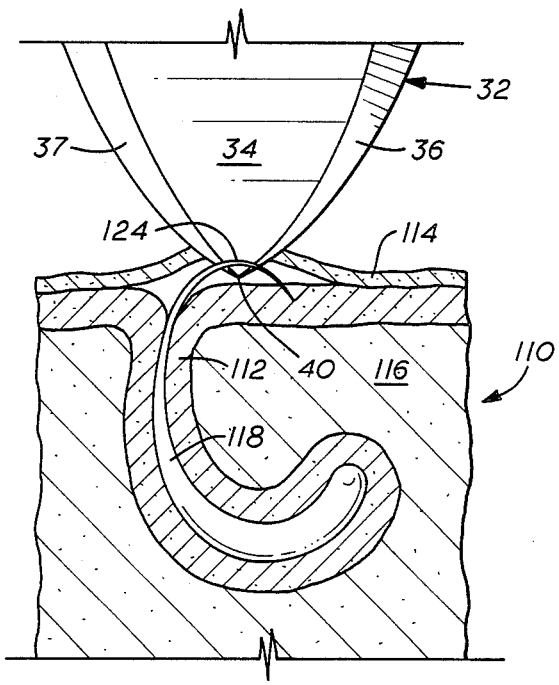
FIG. 5 depicts a cross sectional view of an area of skin having a second form of PFB being extricated by the instrument depicted in FIG. 1.

Similarly, as shown in FIG. 5, the instrument 10 of the present invention can be used to extricate a PFB even where no portion of the pFB is exposed. In this instance, point 40 is used to puncture the epidermis 114 and lift the imbedded portion 124 of hair 118, so that hair 118 protrudes through and out of epidermis 114. With the PFB thus extricated and exposed in the manner described and illustrated in either FIG. 4 or FIG. 5, the surrounding skin area can be treated to relieve or cure any inflammation or infection, and the now-upstanding, normal hair can be shaved in any conventional manner.

The instrument of the present invention is medically and functionally an improvement over the prior art devices used for PFB treatment. The instrument of the present invention provides a means to grasp and extricate an ingrown hair or PFB, both in instances where the PFB is exposed, and where it is entirely under the skin. The instrument of the present invention accomplishes this function in a sanitary and efficient manner. The device can be made at low cost, and packaged in medically sanitary and sealed cellophane packets or the like such that the device would not have to be exposed to the air or surrounding environment until the time it is used. The instrument is large enough to easily be stored or dipped in alcohol or the like between uses, in order to maintain proper sanitation. One skilled in the art will appreciate that the foregoing list of attributes and advantages is not exhaustive of the desirable features of the present invention. It will also be appreciated that modifications to the presently-described preferred embodiment of the invention can be made without departing in substance from the spirit of the invention. Such modifications could include, for example, molding a second tip portion on the end of the handle 12 opposite present tip portion 19, such as at 11. Additionally, the tip portion 19 could be manufactured separately from handle 12, with tip portion 19 and handle 12 being provided with mating and locking means for securing tip 19 to the handle 12. This would enable handle 12 to be reusable indefinitely, with tip 19 being disposable and replace when point 40 dulls, or when sanitary considerations so indicate. One skilled in the art will no doubt think of numerous other such modifications.

What is claimed is:

1. An instrument for use in extricating ingrown hairs from skin tissues, comprising:
    a handle;
    a curved extension attached to said handle, said curved extension having a proximal portion and a distal portion, said distal portion comprising a tapered blade terminating in a sharp point, said tapered blade having a noncutting upper surface adapted for lifting but not cutting the ingrown hairs, said tapered blade further comprising an upper concave surface having radius R, two lower convex surfaces, and two upper side surfaces, all of said surfaces intersecting at said point.

2. An instrument for use in treating PFB by lifting and extricating an ingrown hair, comprising:
an elongate handle;
a tip atached to said handle, said tip comprising a distal portion and a proximal portion, and wherein said distal portion comprises a curved and tapered blade having a noncutting upper surface adapted for lifting but not cutting the ingrown hair, said blade further comprising an upper concave surface of radius R, two lower convex surfaces, said lower convex surfaces intersecting in a crown, and two upper side surfaces, each one of said upper side surfaces intersecting said upper concave surface and a different one of said lower convex surfaces, wherein said upper concave surface, said lower convex surfaces, and said upper side surfaces all intersect and terminate at a sharp point.

3. An instrument according to claim 2, wherein said proximal portion comprises an upper concave surface of radius R, said upper concave surface of said proximal portion being continuous with said upper concave surface of said blade, a lower surface, and two side surfaces.

4. An instrument according to claim 3, wherein said handle comprises an upper surface, a lower surface, and two side surfaces, said lower surface of said handle being substantially coplanar with said lower surface of said proximal portion of said tip, and said side surfaces of said handle being substantially coplanar with the respective side surfaces of said proximal portion of said tip.

5. An instrument according to claim 4, wherein said point is disposed at a predetermined distance above the plane which includes said upper surface of said elongate handle.

6. An instrument according to claim 5, wherein said predetermined distance above said upper surface of the handle exceeds about 0.06 inches.

7. An instrument according to claim 2, wherein said crown which includes the intersection of said two lower convex surfaces has a radius R.

8. An instrument according to claim 2, wherein said instrument is made of nontoxic and hypoallergenic plastic.

9. An instrument according to any one of claims 2, 3, or 7 wherein said radius R exceeds about 0.3 inches.

10. An instrument according to claim 1, wherein said handle comprises an elongate member having a generally rectangular cross section, said elongate member having an upper surface and a lower surface and two side surfaces.

11. An instrument according to claim 10, wherein one end of said proximal portion of said curved extension comprises a cross section identical to said cross section of said handle.

12. An instrument according to claim 1, wherein said two lower convex surfaces intersect, forming a curved crown.

13. An instrument according to claim 12, wherein the radius of said curved crown formed by the intersection of said two lower convex surfaces is substantially equal to R.

14. An instrument according to claim 1, wherein said instrument is made of nontoxic and hypoallergenic plastic.

15. An instrument according to any one of claims 1 or 13, wherein R exceeds about 0.3 inches.

16. An instrument according to claim 10, wherein said point is disposed at a predetermined distance above the plane which includes said upper surface of said elongate member.

* * * * *